United States Patent [19]
Balme et al.

[11] 3,947,493
[45] Mar. 30, 1976

[54] PROCESS FOR THE PRODUCTION OF MALEAMIC ACIDS

[75] Inventors: Maurice Balme, Sainte-Foy-les-Lyon; Max Gruffaz, La Mulatiere, both of France

[73] Assignee: Rhone-Poulenc, S.A., Paris, France

[22] Filed: Oct. 5, 1973

[21] Appl. No.: 403,853

[52] U.S. Cl.......... 260/518 R; 260/308 R; 260/393; 260/514 J; 260/519; 260/534 R; 260/534 E
[51] Int. Cl.²......................................... C07C 99/00
[58] Field of Search ........ 260/518 R, 534 R, 534 E, 260/519, 393, 308 R

[56] References Cited
OTHER PUBLICATIONS
Fieser, L. F. *Reagents for Organic Synthesis*, (1967) pub. by John Wiley & Sons, Inc., p. 845.

*Primary Examiner*—Richard L. Raymond
*Attorney, Agent, or Firm*—Stevens, Davis, Miller & Mosher

[57] ABSTRACT

Maleamic acids of formula:

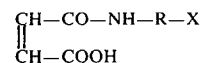

where R is a divalent organic radical and X is H or NHCOCH=CHCOOH are prepared in suspension as a flowing non-thixotropic fluid by a process wherein a solution of a primary monoamine or diamine in a solvent is run into a solution of maleic anhydride in a solvent in an amount such that there is an anhydride excess of 5 to 20 mol % relative to the theoretical amount necessary for the reaction with the amine, the mixture is agitated, the reaction temperature is 40° to 130°C., the time taken to run in the amine solution is at least 67 minutes, and the amine solution is run in at a rate such that the slope of the curve representing the variation, as a function of time, in the rate of running in as % of the total amount of amine solution employed per minute (acceleration) has, at every point on this curve, a value not greater than 0.044.

6 Claims, 1 Drawing Figure

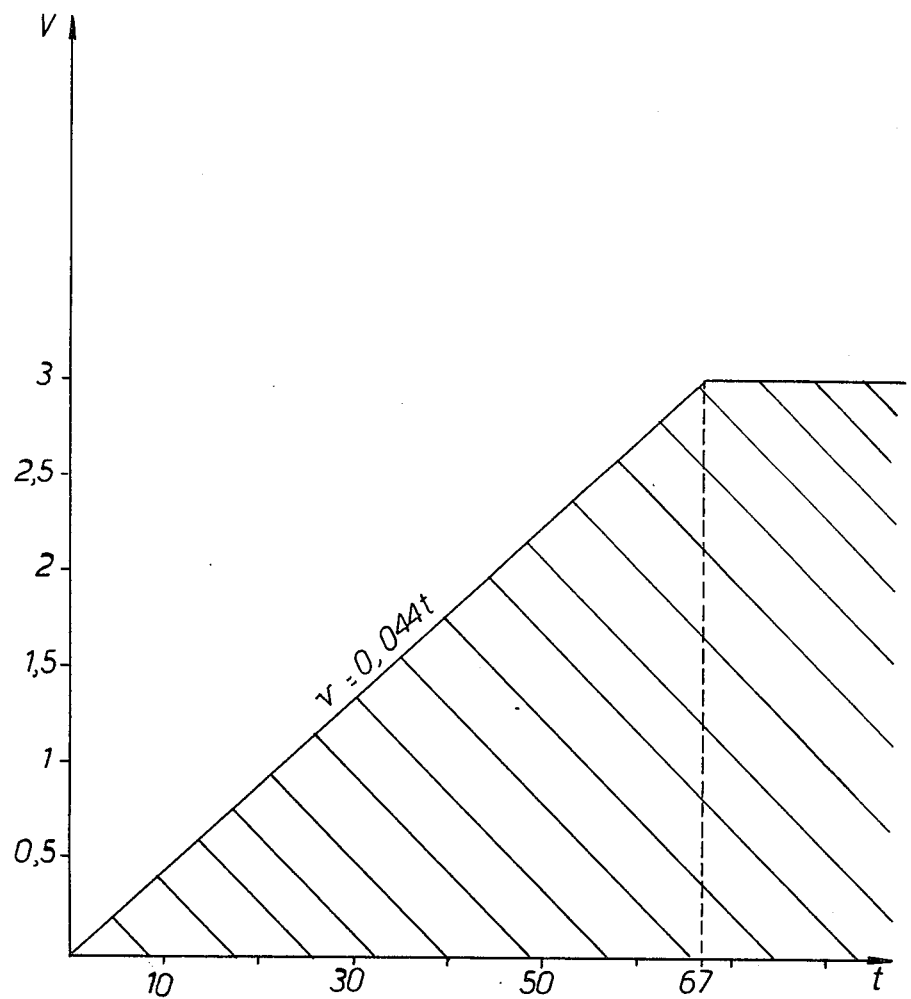

PROCESS FOR THE PRODUCTION OF MALEAMIC ACIDS

The present invention relates to a process for the preparation of maleamic acids in suspension.

Various processes for the preparation of maleamic acids are known including those described in U.S. Pat. Nos. 2,444,536 and 2,723,991 and in the work by L. A. Flett and W. H. Gardner entitled "Maleic Anhydride Derivatives".

One of these known processes involves reacting maleic anhydride with a primary amine in the presence of an organic diluent which makes it possible to remove the heat produced by the exothermic reaction. In this way, a very viscous, thixotropic dispersion which is difficult to pour is obtained and from which the maleamic acid produced can be isolated only with great difficulty by means of the usual processes.

We have now found a new process for the preparation, in suspension, of maleamic acids which has, especially in the case of bis-maleamic acids, numerous advantages both with regard to the ease with which the reaction can be carried out either discontinuously or continuously and the ease with which the maleamic acid can be isolated.

The present invention provides a process for the preparation, in suspension, of a maleamic acid of the general formula

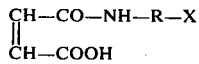

in which: R represents a linear or branched alkylene radical, an arylene radical, an aralkylene radical, an alkylarylene radical, a cycloalkylene radical or a divalent heterocyclic radical, the two free valencies of the heterocyclic radical being carried by carbon atoms, the total number of carbon atoms in the R radical being not more than 20, the minimum number of carbon atoms in the alkylene radical being 2 and X represents either hydrogen or a radical

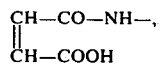

wherein a solution of a primary monoamine or diamine in a solvent is run into a solution of maleic anhydride in a solvent in an amount such that there is an anhydride excess of 5 to 20 mol % relative to the theoretical amount necessary for the reaction with the amine, the mixture is agitated, the reaction temperature is 40° to 130°C., the time taken to run in the amine solution is at least 67 minutes, and the amine solution is run in at a rate such that the slope of the curve representing the variation, as a function of time, in the rate of running in as % of the total amount of amine solution employed per minute (acceleration) has, at every point on this curve, a value not greater than 0.044.

It is also possible, after having manufactured a first quantity of maleamic acid according to the process described above, to proceed with the manufacture continuously by thereafter introducing the reagents simultaneously and continuously into the medium thus produced, heated and stirred, the amine solution being supplied at a rate at most equal to the maximum rate defined above and the anhydride solution in an amount such that the molar ratio anhydride/amine is between 1.05 and 1.2 or 2.1 and 2.4 depending on whether the preparation of a mono- or bis-maleamic acid is involved.

The maleic anhydride is advantageously dissolved in an anhydrous organic solvent such as one of those mentioned below, in proportions such that the concentration of the anhydride solution is between 20 and 30% by weight.

R may be a pure hydrocarbon (or heterocyclic) radical or a hydrocarbon radical interrupted by hetero atoms e.g. —O— or —SO$_2$—. Primary amines which can be used include aniline, ethylene-diamine, hexamethylene-diamine, meta-phenylene-diamine, para-phenylene-diamine, benzidine, diamino-diphenyl-methanes, diamino-diphenyl ethers, diamino-diphenyl-sulphones, diamino-dicyclohexyl-methanes, diamino-dimethylene-cyclohexanes, diamino-meta-xylylenes, diamino-para-xylylenes, diamino-diphenyl-cyclohexanes, diamino-diphenyl-propanes, diamino-triphenyl-ethanes, diamino-triphenyl-methanes and diamino-triazoles.

Of the organic solvents which can be used, those which have a boiling point of between 40°C and 130°C are very suitable. Such solvents include hydrocarbons such as benzene, toluene and cyclohexane, chlorinated hydrocarbons such as chlorobenzene or methylene chloride, cyclic or non-cyclic ethers such as tetrahydrofurane, dioxane or ethyl ether, and dialkyl ketones, such as acetone or methyl ethyl ketone.

The solvent for the primary amine is conveniently the same as that which is used for dissolving the anhydride or, optionally, another solvent from the above list but one which is miscible with the first solvent. Its proportion is preferably such that the final concentration of the maleamic acid dispersion is between 25 and 40% by weight. The presence of a small amount of water in the amine solution can improve the yields slightly, but it is not absolutely necessary.

Agitation of the reaction mixture is advantageously carried out for the entire duration of the reaction with a central stirrer revolving at a rate of the order of 100 to 500 revolutions/minute. Of course, however, any type of stirrer can be used and other rates of stirring can be used.

It has been found that the total duration of the running-in process must be a minimum of 67 minutes, no matter what the amounts of reagents employed may be. However, for economic reasons, the maximum duration does not usually exceed 48 hours.

The curve representing the running-in procedure must be located within the crosshatched area on the FIGURE, of the accompanying drawing where:

The time ($t$), expressed in minutes, to run in the amine solution employed in the reaction is plotted as the abscissa, and the rate of running in $v$, expressed as % per minute of the amount of amine solution, is plotted as the ordinate.

The crosshatched area is delimited by the abscissa axis, by the straight line of equation $v = 0.044\ t$, which corresponds to the case where the rate of running-in increases uniformly from the value 0 at time 0 to the maximum rate of 3%/minute at time 67 minutes, and by the straight line of the equation $v = 3\%$.

This process makes it possible to obtain a fluid suspension which possesses good flow properties and is nonthixotropic, and the viscosity of which is practically that of the solvent.

Furthermore, this suspension separates out rapidly and easily if it is left to stand, making it possible to isolate the maleamic acid from the solvent medium easily by simple filtration.

The Examples which follow are given to illustrate the invention.

EXAMPLE 1

9.07 g of maleic anhydride and 30.07 g of acetone are introduced into a 250 cm³ reactor which is equipped with a central stirrer, a thermometer, a dropping funnel and a reflux condenser, and which is heated by a thermostatically controlled bath. The maleic anhydride dissolves in the acetone. When the temperature of the solution reaches 56.5°C, a solution consisting of:
16.25 g of moist acetone containing 0.7 g of water and 8.89 g of 4,4′-diamino-diphenyl-methane,
is poured in with constant stirring (290 revolutions/minute).

This running-in is carried out in accordance with the following procedure:

| Time elapsed since start of running-in | % of solution run in |
|---|---|
| 15 mins. | 5% |
| 30 mins. | 18% |
| 45 mins. | 44% |
| 60 mins. | 71% |
| 75 mins. | 87% |
| 90 mins. | 100% |

The temperature, which is 56.5°C at the start of the running-in process, is 55.5°C at the end of the process.

The suspension remains very fluid for the entire duration of the reaction.

By leaving the suspension to cool without stirring it, rapid sedimentation of the product formed takes place and the latter can thus be isolated by simple filtration. The yield is 99% of bis-maleamido-diphenyl-methane acid (molecular weight: 397.5, measured by acidimetry).

The viscosity of the dispersion is practically that of the solvent.

EXAMPLE 2

27.2 g of maleic anhydride and 90.2 g of acetone are introduced into a 1 liter reactor which is equipped with a central stirrer, a thermometer, a dropping funnel and a reflux condenser, and which is heated by a bath thermostatically set at 80°C. The maleic anhydride dissolves in the acetone. When the temperature of the solution reaches 56.5°C, a solution consisting of 26.67 g of 4,4′-diamino-diphenyl-methane and 48.75 g of moist acetone containing 2.1 g of water is run in.

This running-in is carried out in accordance with the following procedure:

| Time elapsed since start of running-in | % of solution run in |
|---|---|
| 15 mins. | 1.7% |
| 30 mins. | 3.3% |
| 45 mins. | 15% |
| 60 mins. | 23.6% |
| 75 mins. | 30% |
| 90 mins. | 45% |
| 105 mins. | 100% |

The suspension remains very fluid for the entire duration of the reaction. If the suspension is allowed to cool without being stirred, rapid sedimentation of the product formed takes place and the latter can thus be isolated by simple filtration. The yield obtained is approximately 99% of bis-maleamido-diphenylmethane acid (molecular weight: 397, measured by acidimetry).

EXAMPLE 3

In a 1 liter glass flask equipped with a central stirrer, a thermometer, a reflux condenser and two upper tubes and one lower tube, a suspension of bis-maleamic acid is first prepared by carrying out the following procedure:

221.1 cm³ of a solution of 45.63 g of maleic anhydride in acetone are introduced; this solution is heated to 56.5°C and then 138.9 cm³ of a solution consisting of 44.37 g of 4,4′-diamino-diphenyl-methane and 81.33 g of moist acetone containing 3.48 g of water are added to it. Stirring is kept constant at 290 revolutions/minute for the entire duration of the running-in process. This addition is carried out over the course of 90 minutes in accordance with the procedure given in Example 1.

The two solutions of reagents are then introduced by means of volumetric pumps, one of which delivers the diamine solution at the rate of 166.5 cm³/hour and the other of which delivers the anhydride solution at the rate of 265.5 cm³/hour, into the above suspension which is constantly stirred and heated at 56.5°C. The anhydride solution contains 23.3% by weight of maleic anhydride in acetone, whilst the amine solution, which is also a solution in acetone, contains 35.3% by weight of 4,4′-diamino-diphenyl-methane and 4.3% of water. The delivery rate of each pump is constant with time.

The average dwell time of the bis-maleamic acid dispersion in the reactor is 50 minutes.

The bis-maleamic acid dispersion formed remains very fluid for the entire duration of the experiment and flows out easily via the lower tube of the reactor into a receiving flask where sedimentation takes place spontaneously.

We claim:
1. In a process for the preparation, in suspension, of a maleamic acid of the general formula:

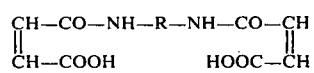

in which: R represents a linear or branched alkylene radical, an arylene radical, an aralkylene radical, an alkylarylene radical, a cyclo-alkylene radical or a divalent heterocyclic radical, the two free valencies of the heterocyclic radical being carried by carbon atoms, the total number of carbon atoms in the R radical being not more than 20, the minimum number of carbon atoms in the alkylene radical being 2, from a solution of primary diamine in a solvent and a solution of maleic anhydride in a solvent, the improvement wherein
  the solution of the primary diamine is run into the solution of maleic anhydride in an amount such that there is an anhydride excess of 5 to 20 mol % relative to the theoretical amount necessary for the reaction with the amine,
  the mixture is agitated,
  and the reaction temperature is 40° to 130°C,
  such that the time taken to run in the amine solution is at least 67 minutes, and the amine solution is run in at a rate such that the slope of the curve representing the variation, as a function of time, in the rate of running in as % of the total amount of amine solution employed per minute has, at every point on this curve, a value not greater than 0.044.

2. A process according to claim 1, wherein the primary amine is 4,4'-diamino-diphenyl-methane.

3. A process according to claim 1 wherein the molar ratio of anhydride to amine is 2.1:1 to 2.4:1.

4. A process according to claim 1 wherein the anhydride solution contains 20–30% by weight anhydride.

5. A process according to claim 1 wherein the solvent has a boiling point of 40°–130°C.

6. A process according to claim 5, wherein the solvent for the primary amine and for maleic anhydride is acetone.

* * * * *